United States Patent
Müller et al.

(10) Patent No.: US 12,396,920 B2
(45) Date of Patent: Aug. 26, 2025

(54) DEVICE FOR ASSISTING A FIRST AIDER WITH A CARDIOPULMONARY RESUSCITATION

(71) Applicant: Smartresq APS, Svendborg (DK)

(72) Inventors: Michael Müller, Freiburg (DE); Matthias Roth, Freiburg (DE); Per Schorling, Svendborg (DK)

(73) Assignee: Smartresq APS, Svendborg (DK)

( * ) Notice: Subject to any disclaimer, the term of this patent is extended or adjusted under 35 U.S.C. 154(b) by 633 days.

(21) Appl. No.: 17/605,257

(22) PCT Filed: Mar. 27, 2020

(86) PCT No.: PCT/IB2020/052915
§ 371 (c)(1),
(2) Date: Oct. 21, 2021

(87) PCT Pub. No.: WO2020/217115
PCT Pub. Date: Oct. 29, 2020

(65) Prior Publication Data
US 2022/0192918 A1 Jun. 23, 2022

(30) Foreign Application Priority Data
Apr. 23, 2019 (DE) .......................... 102019110455.6
Jul. 23, 2019 (DE) .......................... 102019119855.0

(51) Int. Cl.
*A61H 31/00* (2006.01)
*A61N 1/39* (2006.01)

(52) U.S. Cl.
CPC .......... *A61H 31/005* (2013.01); *A61H 31/007* (2013.01); *A61N 1/39044* (2017.08);
(Continued)

(58) Field of Classification Search
CPC .......... A61N 1/39044; A61H 2031/002; A61H 2201/5084; A61H 2201/5097; A61H 2230/04
(Continued)

(56) References Cited

U.S. PATENT DOCUMENTS 9,844,343 B2 * 12/2017 Frey .................... A61B 5/14865
2007/0299473 A1 * 12/2007 Matos ................... A61N 1/3904
607/9
(Continued)

FOREIGN PATENT DOCUMENTS

CN 106902462 A 6/2017
DE 602004002147 T2 12/2004
(Continued)

*Primary Examiner* — Michael J Lau
(74) *Attorney, Agent, or Firm* — Michael Soderman

(57) ABSTRACT

The invention relates to a device for assisting a first aider with a cardiopulmonary resuscitation of a person suffering cardiac arrest, comprising a transport housing (1), in which a sensor apparatus (4) and two adhesive electrodes (2), which are or can be connected to the sensor apparatus (4), can be stowed. The sensor apparatus (4) allows data to be acquired while the first-aid measures for resuscitation are performed. The sensor apparatus (4) comprises an adhesive (5) for attachment to the chest of the patient (3). The chest compressions, i.e. depth of compression and compression frequency, can be detected by means of a motion sensor. An interface for data transfer allows wireless communication with a mobile terminal (6). Furthermore, the sensor apparatus (4) contains a high-voltage store so that, after connection to the adhesive electrodes (2), a single defibrillation shock can be delivered.

8 Claims, 1 Drawing Sheet

(52) U.S. Cl.
CPC .............. *A61H 2031/002* (2013.01); *A61H 2201/5084* (2013.01); *A61H 2201/5097* (2013.01); *A61H 2230/04* (2013.01)

(58) Field of Classification Search
USPC .......................................................... 607/3
See application file for complete search history.

(56) References Cited

U.S. PATENT DOCUMENTS

| | | | | |
|---|---|---|---|---|
| 2008/0312708 | A1* | 12/2008 | Snyder | A61N 1/3904 607/5 |
| 2010/0063559 | A1* | 3/2010 | McIntyre | A61N 1/3904 607/5 |
| 2010/0256539 | A1* | 10/2010 | Strand | A61M 15/0086 600/534 |
| 2011/0224746 | A1* | 9/2011 | Didon | A61B 5/7207 607/5 |
| 2015/0046175 | A1* | 2/2015 | Jorgenson | A61N 1/3925 705/2 |
| 2016/0287470 | A1* | 10/2016 | Lewis | A61N 1/3925 |
| 2017/0259054 | A1 | 9/2017 | Dascoli | |
| 2018/0161238 | A1* | 6/2018 | Dussault | A61H 31/006 |
| 2018/0169426 | A1* | 6/2018 | Montague | A61N 1/3981 |

FOREIGN PATENT DOCUMENTS

| | | | | |
|---|---|---|---|---|
| EP | 2228097 | A1 * | 9/2010 | ............ A61N 1/39 |
| EP | 2255845 | A1 | 12/2010 | |
| EP | 1128795 | B1 | 5/2013 | |
| EP | 1858472 | B1 | 8/2013 | |
| EP | 2653146 | A1 * | 10/2013 | ......... A61H 31/005 |
| WO | 2006104977 | A2 | 10/2006 | |
| WO | WO-2013128306 | A1 * | 9/2013 | ......... A61N 1/3925 |
| WO | WO-2019015727 | A1 * | 1/2019 | ......... A61H 31/005 |

\* cited by examiner

DEVICE FOR ASSISTING A FIRST AIDER WITH A CARDIOPULMONARY RESUSCITATION

CROSS REFERENCE TO RELATED APPLICATIONS

This application is the U.S. national stage of International Application No. PCT/162020/052915, filed on 2020 Mar. 27. The international application claims the priority of DE 102019110455.6 filed on 2019 Apr. 23 and the priority of DE 102019119855.0 filed on 2019 Jul. 23; all applications are incorporated by reference herein in their entirety.

BACKGROUND

The invention concerns an apparatus for collecting data and for instructing a helper in the implementation of first aid measures for resuscitation of a patient affected by cardiac arrest according to the preamble of claim 1.

Survival after sudden cardiac death is only possible if, within the first minutes, hence usually still before the arrival of the rescue service, a cardiac massage is performed and is carried out in accordance with the respective current recommendations of the guidelines. The patient must also be ventilated. The delivery of a defibrillation shock within the first minute in the presence of ventricular fibrillation or ventricular tachycardia also increases the probability of survival to approx. 90%.

For example, in Germany, in only about 40% of emergencies, lay helpers initiate the important measures of resuscitation (especially cardiac massage). The quality of the cardiac massage is good after education and practical training, but it decreases again considerably after three to six months. In addition, the quality of the cardiac massage decreases considerably after just two minutes during a resuscitation. Carrying out a cardiac massage also triggers considerable stress reactions, at least in the lay helper, in which an instruction from the helper can improve the quality of the cardiac massage.

The probability of survival of a patient with cardiac arrest depends essentially on the first aid measures of the lay helper, who is often overwhelmed with the situation, and who is rarely adequately trained. Even with trained lay helpers, the quality of the measures is often inadequate. For this reason, systems that support resuscitation are very helpful for the helper.

From EP 1 128 795 B1 a system is known for measuring and applicating chest compressions. It includes a mobile CPR compression monitor (CPR-cardiopulmonary resuscitation, heart-lung resuscitation) for monitoring the thorax compressions during resuscitation of a person affected by cardiac arrest. The apparatus is placed on the hand of the helper or on the patient and includes acceleration sensors as well as an interface for data transmission. An evaluation unit integrated in the CPR compression monitor or an independent evaluation unit with a display screen is connected to this interface via a cable. This system is designed for trained and experienced medical personnel.

WO 2006/104977 A2, EP 2 255 845 A1 and DE 60 2004 002 147 T2 disclose a multi-layered professional medical system for supporting a first aider, who must be educated in resuscitation. The system includes, among others, a defibrillator and a mobile display and control device.

EP 1 858 472 B1 also describes a mobile, but very complex medical system for supporting a helper during resuscitation, which also comprises a defibrillator. It is planned to station the apparatus in a few central locations with a high number of people such that first aiders have quick access to it. However, this apparatus can only be used reasonably well by educated helpers.

Another disadvantage of the above apparatus is their size and their weight, which make a day in-day out carrying impossible, such that these apparatuses e.g. are stored in central places. However, in an emergency, a first aider often does not know where to find such a first aid apparatus, or valuable minutes pass before the apparatus is brought in. A (first) aider is also often overwhelmed, especially if he has not been adequately trained on the respective apparatus before the occurrence of the emergency.

Particularly in systems with an automatic defibrillator, it has also been shown that, until the start of the first cardiac massage, a comparatively large amount of time—on average just under two minutes—is lost due to preparatory measures. However, this contradicts the recommendations for resuscitation measures, according to which cardiac massage should be performed as soon as possible, i.e. after less than 30 seconds.

SUMMARY

It is the object of the invention to provide an apparatus for supporting a first aider during cardiopulmonary resuscitation, which comprises a sensor device for collecting data when performing first aid measures for resuscitation, wherein the apparatus should be so small and compact that it can always be carried by any lay person or first aider willing to help, and wherein the handling should be absolutely intuitive, such that it can be used for immediate resuscitation, also in stressful situations, by an uneducated lay helper, who has no previous medical knowledge.

The object is achieved by an apparatus to support a first aider with the characterising features according to claim 1; appropriate embodiments of the invention can be found in the dependent claims.

DETAILED DESCRIPTION

According to the invention, an apparatus for assisting a first aider in a resuscitation is provided, which, due to its dimensions and its weight, can be carried day in-day out, e.g. in a handbag. The apparatus comprises a sensor device, including sensors for recording the data relevant to the cardiac massage, as well as electrodes for measuring the patient's EKG data and for delivering defibrillation shocks.

The apparatus is designed to support first aiders, but also in particular insufficiently educated lay helpers, in the resuscitation of patients with cardiac arrest.

The apparatus according to the invention comprises a preferably rigid transport housing in which the sensor device, cables and at least two electrodes are stored. This transport housing can be designed as a two-part, flat box, for example in the form of a key ring. The outer dimensions are preferably within 10 cm×10 cm×3 cm.

The transport housing is designed, based on its choice of materials and/or its structure, as an at least splash-proof container that allows a protected, e.g. from dirt, storage of its contents for at least four years.

The sensor device comprises a motion sensor, a storage for electrical energy, hereinafter referred to as a battery, a microprocessor, a high-voltage storage (e.g. in the form of a capacitor) for a defibrillation pulse, terminals for the electrodes, an interface for transmitting and/or receiving data and/or commands as well as an adhesive on its outer shell for attaching the sensor device to the chest of the patient.

On one side, the electrodes have an adhesive surface covered with a removable protective film. In addition, the electrodes may have kinked folds such that they can be folded up during storage in the transport housing. By means of the electrodes, electrical currents/voltages are recorded, e.g. to record an electrocardiogram (EKG), and/or transmit a defibrillation shock to the patient. The electrodes can be connected to the sensor device by means of the cables.

The microprocessor is designed in such a way that the data recorded by means of the sensors and electrodes can be evaluated and processed in a form that can be displayed or further processed by a mobile apparatus wirelessly or by means of a cable connected via the interface with the sensor device. The mobile terminal communicating with the sensor device can be any type of commercially available portable small or micro computer, for example a smartphone, a phablet, a tablet or a smartwatch, the mobile terminal itself not being part of the invention.

The mobile terminal connected to the sensor device receives data and gives the first aider instructions for optimal resuscitation via application software to be installed on the terminal. The software running on the terminal can combine data from the electrodes and the sensor device in order to achieve valid results. For example, impedances (from the electrodes) together with movement data from the position and/or movement sensor can enable the helper to make a valid assessment of spontaneous breathing or ventilation. In this way, the first aider receives feedback on the quality of the measures he has taken, in particular the cardiac massage, and a message if a defibrillation shock is necessary.

In the sensor device—either remotely controlled from the connected terminal or immediately after switching on the sensor device—a defibrillation shock is prepared, i.e. the high-voltage storage, e.g. in the form of a capacitor, is charged. After automatic triggering by the mobile terminal and/or manual triggering by the first aider using a trigger button on the sensor device and/or via an option in the software running on the mobile terminal, the current from the high-voltage storage is delivered to the patient as a defibrillation shock. For example, the triggering of the shock is prepared automatically by the software running on the mobile apparatus, with the triggering first having to be confirmed by the first aider by pressing the trigger button on the sensor device.

Due to the size of the sensor device, the battery and the high-voltage storage are dimensioned to generate at least one, but, if possible, two or three defibrillation shocks. Although the apparatus does not meet the usual requirements for an (automated) external defibrillator, since the necessary external dimensions would prevent a constant carrying (for example in the handbag or jacket pocket), but it can enable successful resuscitation by delivering at least one defibrillation shock, when it is generated fast enough.

The advantage of the invention is that the apparatus, in comparison to the medical apparatuses known from the prior art for supporting a first aider during resuscitation (especially those with an additional defibrillator), is very small and therefore easily transportable. In addition, due to its smaller size, it is also significantly cheaper, such that it can be used more widely—especially is accessible to everyone. Since the apparatus can be carried, due to its size, e.g. in the glove compartment of a motor vehicle, it is immediately available in emergency situations and, accordingly, a possibly necessary defibrillation shock can be delivered within less than 2 minutes. The apparatus is designed to provide support in the first few minutes of emergency supply. It can—if necessary—trigger a defibrillation shock, but is in no way intended to replace a defibrillator. Occasionally, as part of the resuscitation, multiple or even many defibrillation shocks are necessary, such that an additional external defibrillator must be used if the resuscitation with the apparatus described here is not successful within a few minutes.

A further advantage is that the necessary processes—such as deriving the heart currents, the analysis and interpretation of the measurement data, the instruction of the first aider in the emergency measures and (possibly in combination with a switch to be operated on the apparatus) the triggering of the defibrillation shock—can be adopted by the terminal connected to the sensor device. This embodiment of the invention makes it possible to build the apparatus, i.e. the hardware required in addition to the already existing mobile apparatus (e.g. a standard commercial Android smartphone), in an extremely small form. In the ideal case, operating elements and a display unit can be dispensed with in the sensor device of the apparatus.

By means of software running on the mobile terminal (application program), the EKG obtained via the electrodes is evaluated, among other things, and a decision is made as to whether a shock should be delivered. If appropriate, the defibrillation is integrated by the software into the instruction for the first aider. The EKG as well as the data on the delivered defibrillation shock can be saved and transmitted to the medical facility, which takes care of the patient.

The invention can further be designed such that it comprises an activation apparatus by means of which the sensor device is switched on, i.e. at least the microprocessor and the high-voltage storage are connected to the battery. This activation apparatus can be a manually-operated toggle switch or a push button.

The sensor device can also include a positioning tool in the form of an extendable or fold-out band of a predetermined length, such that after applying the extended/unfolded positioning tool on the sternum, the sensor device is at the optimal position on the chest for cardiac massage.

It can be provided that the positioning tool is coupled to the activation apparatus or represents the latter, such that by actuating the positioning tool, the sensor device can be activated at the same time.

Alternatively, it can be provided that the activation apparatus is a pressure- or movement-sensitive activation switch which is arranged within the housing of the sensor device and which activates the sensor device as soon as the first aider applies pressure to it.

According to a preferred embodiment, the interface of the sensor device for communication with a mobile terminal is a wireless interface, which can be designed according to a Bluetooth standard.

Furthermore, the sensor device can have a pressure or force sensor which, for example, detects complete relief of the chest during the cardiac massage and/or—as already stated—can be used as activation apparatus for the sensor device.

According to an embodiment, the sensor device additionally has a temperature and/or multi-sensor for measuring medical parameters (e.g. impedance of the body). Also a sensor for testing breathing and the quality of ventilation can be provided.

Alternatively, the adhesive is designed as an adhesive coating of a surface area of the sensor device, for example as an adhesive bandage on the back (sticking bandage). In this case, the adhesive surface of the bandage is covered with a removable protective film.

Furthermore, it can be provided that the battery and the high-voltage storage are designed in such a way that exactly one defibrillation shock can be delivered, wherein the residual energy remaining in the battery after delivery of the shock is only sufficient to keep the sensors, the microprocessor and the interface working for about 30 minutes.

On the outside of his housing, the sensor device can, at least on an area of the surface, which comes into contact—with intended use of the sensor device during the reanimation—with e.g. the hand of the reanimator pushing on the chest of the patient, comprise an adhesive surface in the form of an adhesive coating. That is, the sensor device can have, in addition to the adhesive applied on its "bottom side", an additional, adhesive-acting surface area (adhesive surface) on its "top side".

The storage for electrical energy can be a disposable battery or a rechargeable battery cell, wherein the charging of the battery can be done inductively, i.e. in this case the sensor device also includes an inductive charging interface for coupling to an inductive charging device.

According to an embodiment, the movement sensor of the sensor device is an acceleration sensor, for example a three-axis acceleration sensor, wherein from the acceleration values detected by the sensor, both the indentation depth and the compression frequency can be calculated. It can also be provided that the sensor device comprises two, in particular redundant, movement sensors.

The positioning tool can be in the form of a measuring standard, e.g. a band, a cord or a rod of a predetermined length, which can be folded-out or pulled-out of the housing. Preferably, the positioning tool is a flexible measuring standard that can be pulled-out or rolled-out of which the maximum length does not exceed 8 cm, preferably 5 cm.

It can be provided that the measuring standard has marking positions—e.g. designed as snap-in points, each of which define a respective predetermined extension length of the measuring standard when pulling out of the housing of the sensor device—for patients of different body sizes, e.g. in the form of a marker for children, for teenagers and for adult men or women. An exact placement of the sensor device on the patient's chest is made possible by applying the measuring standard to the sternum. In particular, the invention can be designed such that the measuring standard consists of a flexible or rigid fibre reinforced plastic, e.g. carbon-fibre reinforced plastic (CFRP) or of aramid, wherein its temperature-dependent length expansion coefficient can be essentially zero.

Alternatively or additionally, it can be provided that the measuring standard has a one-sided, at least partially applied adhesive layer, such that when the positioning tool is actuated, the measuring body can be fixed on the patient's chest by means of the adhesive layer.

The apparatus for supporting a first aider during cardiopulmonary resuscitation is explained in more detail below with reference to the figures, wherein the same or similar features are provided with the same reference numerals.

BRIEF DESCRIPTION OF THE DRAWINGS

To this end, shows in a schematic representation

DETAILED DESCRIPTION OF THE PREFERRED EMBODIMENTS

Figure 1:
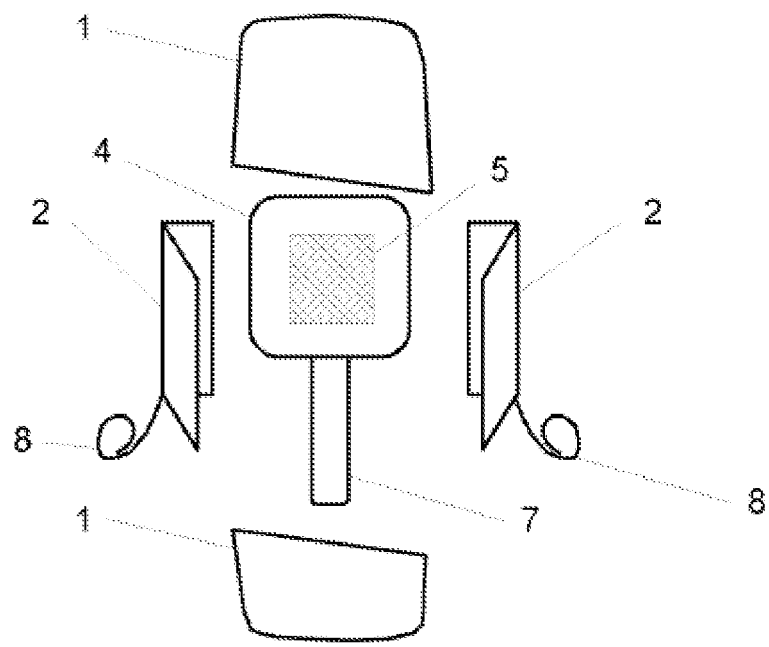
FIG. 1: an embodiment of the apparatus in plan view.

According to FIG. 1, the apparatus comprises the two-part transport housing 1, which is designed here as a waterproof container. In the same the two adhesive electrodes 2 with the cables 8 and the sensor device 4 are situated. In FIG. 1, the positioning tool 7, which has already been pulled out of the sensor device 4, is shown. On the back of the sensor device 4, the adhesive 5 is applied, by means of which the sensor device 4 can be attached to the chest.

Figure 2:
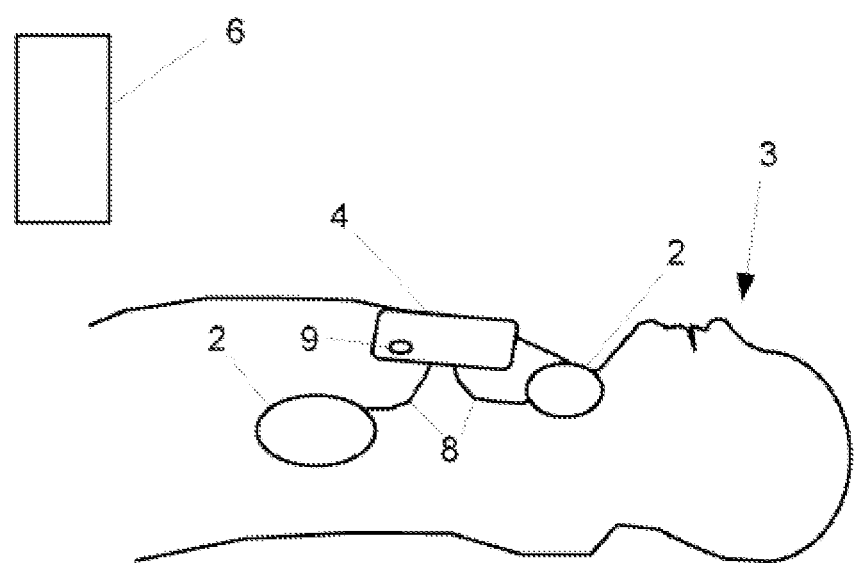
FIG. 2: an application of the apparatus on the patient.

According to FIG. 2, when an emergency occurs, the sensor device 4 and the adhesive electrodes 2 are removed from the transport housing 1. The adhesive electrodes 2 are attached to the chest of the patient 3 and connected to the sensor device 4 by means of the cables 8. The sensor device 4 (here an embodiment without a positioning tool) is switched on by actuating the switch 9, whereby the high-voltage storage (not shown) is also charged, and is subsequently attached to the chest of the patient 3.

The mobile terminal 6, here a smartphone, communicates by means of a wireless interface (here according to the WLAN 802.11ax standard) with the sensor device 4. Software, started on the mobile terminal 6 guides the first aider (not shown), whereby it—when the corresponding indication apply—after the first aider has been informed—automatically triggers a single defibrillation shock.

LIST OF REFERENCE NUMERALS

1 Transport housing
2 Adhesive electrode
3 Patient
4 Sensor device
5 Adhesive
6 Mobile terminal
7 Positioning tool
8 Cable
9 Power switch

The invention claimed is:

1. An apparatus for supporting a first aider in a cardiopulmonary resuscitation, comprising a sensor device, two adhesive electrodes connectable or connected with the sensor device and a largely flat transport housing in which the sensor device and the two adhesive electrodes are storable, wherein the sensor device comprises
    a top side that contacts a hand of the first aider when the sensor device is used as intended, and a bottom side opposite the top side,
    a storage for electrical energy, a microprocessor and a high-voltage storage with terminals for the adhesive electrodes,
    an activation apparatus for connecting at least the microprocessor and the high-voltage storage to the storage for electrical energy,
    a movement sensor and
    an interface for sending and/or receiving data and/or commands,
characterized in that
    the transport housing is rigid and has geometric external dimensions of at most 10 cm×10 cm×3 cm,
    the bottom side of the sensor device has an adhesive substance arranged on a surface area for fastening the sensor device on the chest of a patient or a training mannequin,
    the adhesive electrodes comprised kinked folds, by which the adhesive electrodes are folded during storage in the transport housing,
    the storage for electrical energy and the high-voltage storage are designed in such a way that exactly only one defibrillation shock can be delivered, wherein residual energy remaining in a battery after delivery of the shock is only sufficient to keep the sensors, the microprocessor and the interface working for about 30 minutes.

2. The apparatus according to claim 1, characterized in that at least one surface area of the top side of the sensor device comprises an adhesive coating or an adhesive material.

3. The apparatus according to claim 1, characterized in that the interface is wireless.

4. The apparatus according to claim 1, characterized in that the storage for electrical energy is rechargeable, wherein the sensor device has an inductive charging interface for an inductive charging device.

5. The apparatus according to claim 1, characterized in that the motion sensor is an acceleration sensor.

6. The apparatus according to claim 1, characterized in that the adhesive substance is an adhesive bandage, the adhesive surface of which is covered with a removable protective film.

7. The apparatus according to claim 1, characterized in that it has a positioning tool connected to the sensor device for the exact positioning of the sensor device on the sternum.

8. The apparatus according to claim 7, characterized in that the positioning tool is a measuring standard that can be folded-out or pulled-out of the sensor device.

\* \* \* \* \*